United States Patent [19]

Lesher et al.

[11] 4,362,735

[45] Dec. 7, 1982

[54] 3-[(3-OXO-1-BUTENYL)AMINO]-5-(PYRIDINYL)-2(1H)-PYRIDINONES AND THEIR CARDIOTONIC USE

[75] Inventors: George Y. Lesher, Schodack; Ruth P. Brundage, East Greenbush, both of N.Y.

[73] Assignee: Sterling Drug Inc., New York, N.Y.

[21] Appl. No.: 297,828

[22] Filed: Aug. 31, 1981

[51] Int. Cl.³ .................... A61K 31/44; C07D 213/74
[52] U.S. Cl. ..................................... 424/263; 546/257
[58] Field of Search ........................ 546/257; 424/263

[56] References Cited

U.S. PATENT DOCUMENTS

| 3,862,161 | 1/1975 | Bossert et al. | 546/257 |
| 4,004,012 | 1/1977 | Lesher et al. | 546/257 |
| 4,072,746 | 2/1978 | Lesher et al. | 546/257 |
| 4,137,233 | 1/1979 | Lesher et al. | 546/257 |

FOREIGN PATENT DOCUMENTS 886336  5/1980  Belgium .

Primary Examiner—Norma S. Milestone
Attorney, Agent, or Firm—Robert K. Blair; B. Woodrow Wyatt; Paul E. Dupont

[57] ABSTRACT

1-$R_1$-3-[(1-Methyl-3-oxo-1-butenyl)amino or (3-oxo-1-butenyl)amino]-5-PY-6-R-2(1H)-pyridinones, where $R_1$ is hydrogen or lower-alkyl, PY is 4- or 3-pyridinyl or 4- or 3-pyridinyl having one or two lower-alkyl substituents and R is hydrogen or lower-alkyl, or pharmaceutically acceptable acid-addition salts thereof are useful as cardiotonic agents. The preparation and cardiotonic use of said compounds are shown.

11 Claims, No Drawings

3-[(3-OXO-1-BUTENYL)AMINO]-5-(PYRIDINYL)-2(1H)-PYRIDINONES AND THEIR CARDIOTONIC USE

BACKGROUND OF THE INVENTION (a) Field of the Invention

This invention relates to 3-amino-5-(pyridinyl)-2(1H)-pyridinone derivatives, their use as cardiotonic agents, and their preparation.

(b) Description of the Prior Art

Lesher and Opalka [U.S. Pat. Nos. 4,004,012, issued Jan. 18, 1977, and 4,072,746, issued Feb. 7, 1978] show, inter alia, as cardiotonic agents 3-amino-5-(pyridinyl)-2(1H)-pyridinones and certain derivatives thereof, e.g., 3-(lower-alkyl)amino, 3-di-(lower-alkyl)amino, 3-(lower-alkanoyl)amino and 3-(carbo-lower-alkoxy)amino.

Belgian Pat. No. 886,336, granted May 25, 1980, shows, inter alia, as cardiotonic agents 3-amino-6-(lower-alkyl)-5-(pyridinyl)-2(1H)-pyridinones and certain derivatives thereof, e.g., 3-(lower-alkylamino), 3-di-(lower-alkyl)amino and 3-(lower-alkanoyl)amino. These compounds also are disclosed and claimed in copending Lesher and Philion patent application Ser. No. 198,461, filed Oct. 20, 1980, a continuation-in-part of application Ser. No. 97,504, filed Nov. 26, 1979 and now abandoned.

SUMMARY OF THE INVENTION

In a composition of matter aspect, the invention resides in the compound, 1-$R_1$-3-[(3-oxo-1-butenyl)- or (1-methyl-3-oxo-1-butenyl)amino]-6-R-5-PY-2(1H)-pyridinone or acid-addition salt thereof, useful as a cardiotonic agent, where R, $R_1$ and PY are defined hereinbelow.

In a process aspect the invention comprises reacting 1-$R_1$-3-amino-6-R-5-PY-2(1H)-pyridinone with n-pentane-2,4-dione to produce 3-[(1-methyl-3-oxo-1-butenyl)amino]-6-R-5-PY-2(1H)-pyridinone.

In another process aspect the invention comprises reacting 1-$R_1$-3-amino-6-R-5-PY-2(1H)-pyridinone with 4-methoxy-3-buten-2-one to produce 1-$R_1$-3-[(3-oxo-1-butenyl)amino]-6-R-5-PY-2(1H)-pyridinone.

A composition aspect of the invention resides in a cardiotonic composition for increasing cardiac contractility, said composition comprising a pharmaceutically acceptable carrier and, as the active ingredient thereof, a cardiotonically effective amount of 1-$R_1$-3-[(3-oxo-1-butenyl)- or (1-methyl-3-oxo-1-butenyl)amino]-6-R-5-PY-2(1H)-pyridinone or pharmaceutically acceptable acid-addition salt thereof.

In a method aspect the invention relates to a method for increasing cardiac contractility in a patient requiring such treatment which comprises administering a medicament comprising a pharmaceutically acceptable carrier and, as the active component thereof, a cardiotonically effective amount of 1-$R_1$-3-[(3-oxo-1-butenyl)- or (1-methyl-3-oxo-1-butenyl)amino]-6-R-5-PY-2(1H)-pyridinone or pharmaceutically acceptable acid-addition salt thereof.

DETAILED DESCRIPTION INCLUSIVE OF PREFERRED EMBODIMENTS

In a composition of matter aspect the invention resides in 1-$R_1$-3-[(3-oxo-1-butenyl)- or (1-methyl-3-oxo-1-butenyl)amino]-6-R-5-PY-2(1H)-pyridinone having the formula I

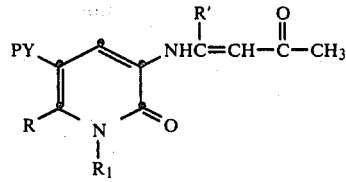

or acid-addition salt thereof, where R' is hydrogen or methyl, $R_1$ and R are each hydrogen or lower-alkyl, PY is 4-pyridinyl or 3-pyridinyl, or 4-pyridinyl or 3-pyridinyl having one or two lower-alkyl substituents. Preferred embodiments are the compounds of formula I where PY is 4- or 3-pyridinyl, R and R' are each hydrogen or methyl and $R_1$ is hydrogen. Particularly preferred embodiments are the compounds of formula I where PY is 4-pyridinyl, R is hydrogen or methyl, $R_1$ is hydrogen and R' is methyl. The compounds of formula I are useful as cardiotonic agents, as determined by standard pharmacological evaluation procedures.

A process aspect of the invention resides in the process for preparing the compound having formula I where R' is methyl which comprises reacting 1-$R_1$-3-amino-6-R-5-PY-2(1H)-pyridinone with n-pentane-2,4-dione.

In another process aspect the invention resides in the process for preparing the compound having formula I where R' is hydrogen which comprises reacting 1-$R_1$-3-amino-6-R-5-PY-2(1H)-pyridinone with 4-methoxy-3-buten-2-one.

A composition aspect of the invention resides in the cardiotonic composition for increasing cardiac contractility, said composition comprising a pharmaceutically acceptable carrier and, as the active component thereof, a cardiotonically effective amount of the compound having formula I or a pharmaceutically acceptable acid-addition salt thereof.

A method aspect of the invention resides in the method for increasing cardiac contractility in a patient requiring such treatment which comprises administering orally or parenterally in solid or liquid dosage form to such patient a cardiotonically effective amount of the compound of formula I or pharmaceutically acceptable acid-addition salt thereof.

The term "lower-alkyl" as used herein, e.g., as one of the meanings for R or R' or as a substituent for PY in formula I, means alkyl radicals having from one to six carbon atoms which can be arranged as straight or branched chains, illustrated by methyl, ethyl, n-propyl, isopropyl, n-butyl, sec.-butyl, tert.-butyl, isobutyl, n-pentyl, n-hexyl, and the like.

Illustrative of PY in formula I where PY is 4- or 3-pyridinyl having one or two lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The compounds having formula I are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention, it is convenient to form the free base form; however, appropriate pharmaceutically acceptable salts within the scope of the invention are those derived from mineral acids such as hydrochloric acid, sulfuric acid, phosphoric acid and sulfamic acid; and organic acid such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, give the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compound are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compound are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structures of the compounds having formula I were assigned on the basis of evidence provided by infrared, nuclear magnetic resonance and mass spectra, by chromatographic mobilities, and by the correspondence of calculated and found values for the elementary analyses.

The manner of making and using the instant invention will now be generally described so as to enable a person skilled in the art of pharmaceutical chemistry to make and use the same, as follows.

The reactions of 1-$R_1$-3-amino-6-R-5-PY-2(1H)-pyridinone with n-pentane-2,4-dione to produce 1-$R_1$-3-[(1-methyl-3-oxo-1-butenyl)amino]-6-R-5-PY-2(1H)-pyridinone and of 1-$R_1$-3-amino-6-R-5-PY-2(1H)-pyridinone with 4-methoxy-3-buten-2-one to produce 1-$R_1$-3-[(3-oxo-1-butenyl)-amino]-6-R-5-PY-2(1H)-pyridinone are carried out by heating the reactants at about 70° to 130° C., preferably about 85° to 115° C. Each reaction is conveniently run by heating the reactants in dimethylformamide on a steam bath. Other suitable aprotic solvents include dioxane, tetrahydrofuran, 1,2-dimethoxyethane, and the like.

The following examples will further illustrate the invention without, however, limiting it thereto.

EXAMPLE 1

3-[(1-Methyl-3-oxo-1-butenyl)amino]-5-(4-pyridinyl)-2(1H)-pyridinone

A mixture containing 41 g. of 3-amino-5-(4-pyridinyl)-2(1H)-pyridinone, 170 ml. of n-pentane-2,4-dione and 850 ml. of dimethylformamide was heated with stirring on a steam bath for seven hours and allowed to cool to room temperature. The crystalline product that separated was collected by filtration, washed successively with ethanol and acetone and dried to yield 29.2 g. of 3-[(1-methyl-3-oxo-1-butenyl)amino]-5-(4-pyridinyl)-2(1H)-pyridinone, m.p. 282°–284° C.

Acid-addition salts of 3-[(1-methyl-3-oxo-1-butenyl)amino]-5-(4-pyridinyl)-2(1H)-pyridinone are conveniently prepared by carefully adding to a mixture of 1 g. of 3-[(1-methyl-3-oxo-1-butenyl)amino]-5-(4-pyridinyl)-2(1H)-pyridinone in about 20 ml. of aqueous methanol the appropriate acid, e.g., methanesulfonic acid, concentrated sulfuric acid, concentrated phosphoric acid, to a pH of about 2 to 3, chilling the mixture after partially evaporating and collecting the precipitated salt, e.g., dimethanesulfonate, sulfate, phosphate, respectively. Also, the acid-addition salt is conveniently prepared in aqueous solution by adding to water with stirring molar equivalent quantities each of 3-[(1-methyl-3-oxo-1-butenyl)amino]-5-(4-pyridinyl)-2(1H)-pyridinone and the appropriate acid, e.g., lactic acid or hydrochloric acid to prepare respectively the monolactate or monohydrochloride salt in aqueous solution.

EXAMPLE 2

3-[(3-Oxo-1-butenyl)amino]-5-(4-pyridinyl)-2(1H)-pyridinone

A mixture containing 24 g. of 3-amino-5-(4-pyridinyl)-2(1H)-pyridinone, 50 ml. of 4-methoxy-3-buten-2-one and 450 ml. of dimethylformamide was heated on a steam bath for twelve hours and then allowed to cool to room temperature. After chilling in an ice bath, the crystalline product was collected by filtration, washed successively with dimethylformamide and ethyl acetate, and then dried to yield 26 g. of 3-[(3-oxo-1-butenyl)amino]-5-(4-pyridinyl)-2(1H)-pyridinone, m.p. > 300° C.

Acid-addition salts of 3-[(3-oxo-1-butenyl)amino]-5-(4-pyridinyl)-2(1H)-pyridinone are conveniently prepared by carefully adding to a mixture of 1 g. of 3-[(3-oxo-1-butenyl)amino]-5-(4-pyridinyl)-2-(1H)-pyridinone in about 20 ml. of aqueous methanol the appropriate acid, e.g., methanesulfonic acid, concentrated sulfuric acid, concentrated phosphoric acid, to a pH of about 2 to 3, chilling the mixture after partially evaporating and collecting the precipitated salt, e.g., dimethanesulfonate, sulfate, phosphate, respectively. Also, the acid-addition salt is conveniently prepared in aqueous solution by adding to water with stirring molar equivalent quantities each of 3-[(3-oxo-1-butenyl)amino]-5-(4-pyridinyl)-2(1H)-pyridinone and the appropriate acid, e.g., lactic acid or hydrochloric acid to prepare respectively the monolactate or monohydrochloride in aqueous solution.

Following the procedure described in Example 1 but using in place of 3-amino-5-(4-pyridinyl)-2(1H)-pyridinone a molar equivalent quantity of the appropriate 1-$R_1$-3-amino-6-R-5-PY-2(1H)-pyridinone, it is contemplated that the following 1-$R_1$-3-[(1-methyl-3-oxo-1-butenyl)amino]-6-R-5-PY-2(1H)-pyridinones of Examples 3–14 can be obtained.

3. 3-[(1-Methyl-3-oxo-1-butenyl)amino]-5-(3-pyridinyl)-2(1H)-pyridinone.

4. 1-Methyl-3-[(1-methyl-3-oxo-1-butenyl)amino]-5-(4-pyridinyl)-2(1H)-pyridinone.

5. 6-Methyl-3-[(1-methyl-3-oxo-1-butenyl)amino]-5-(4-pyridinyl)-2(1H)-pyridinone.
6. 6-Ethyl-3-[(1-methyl-3-oxo-1-butenyl)amino]-5-(4-pyridinyl)-2(1H)-pyridinone.
7. 1,6-Dimethyl-3-[(1-methyl-3-oxo-1-butenyl)amino]-5-(4-pyridinyl)-2(1H)-pyridinone.
8. 3-[(1-Methyl-3-oxo-1-butenyl)amino]-5-(2-methyl-3-pyridinyl)-2(1H)-pyridinone.
9. 3-[(1-Methyl-3-oxo-1-butenyl)amino]-5-(5-methyl-3-pyridinyl)-2(1H)-pyridinone.
10. 3-[(1-Methyl-3-oxo-1-butenyl)amino]-5-(3-ethyl-4-pyridinyl)-2(1H)-pyridinone.
11. 3-[(1-Methyl-3-oxo-1-butenyl)amino]-6-n-propyl-5-(4-pyridinyl)-2(1H)-pyridinone.
12. 6-Ethyl-3-[(1-methyl-3-oxo-1-butenyl)amino]-5-(2-methyl-4-pyridinyl)-2(1H)-pyridinone.
13. 6-Ethyl-3-[(1-methyl-3-oxo-1-butenyl)amino]-5-(3-pyridinyl)-2(1H)-pyridinone.
14. 3-[(1-Methyl-3-oxo-1-butenyl)amino]-5-(2,6-dimethyl-4-pyridinyl)-2(1H)-pyridinone.

Following the procedure described in Example 2 but using in place of 3-amino-5-(4-pyridinyl)-2(1H)-pyridinone a molar equivalent quantity of the appropriate 1-$R_1$-3-amino-6-R-5-PY-2(1H)-pyridinone, it is contemplated that the following 1-$R_1$-3-[(3-oxo-1-butenyl)amino]-6-R-5-PY-2(1H)-pyridinones of Examples 15–26 can be obtained.

15. 3-[(3-Oxo-1-butenyl)amino]-5-(3-pyridinyl)-2(1H)-pyridinone.
16. 1-Methyl-3-[(3-oxo-1-butenyl)amino]-5-(4-pyridinyl)-2(1H)-pyridinone.
17. 6-Methyl-3-[(3-oxo-1-butenyl)amino]-5-(4-pyridinyl)-2(1H)-pyridinone.
18. 6-Ethyl-3-[(3-oxo-1-butenyl)amino]-5-(4-pyridinyl)-2(1H)-pyridinone.
19. 1,6-Dimethyl-3-[(3-oxo-1-butenyl)amino]-5-(4-pyridinyl)-2(1H)-pyridinone.
20. 3-[(3-Oxo-1-butenyl)amino]-5-(2-methyl-3-pyridinyl)-2(1H)-pyridinone.
21. 3-[(3-Oxo-1-butenyl)amino]-5-(5-methyl-3-pyridinyl)-2(1H)-pyridinone.
22. 3-[(3-Oxo-1-butenyl)amino]-5-(3-ethyl-4-pyridinyl)-2(1H)-pyridinone.
23. 3-[(3-Oxo-1-butenyl)amino]-6-n-propyl-5-(4-pyridinyl)-2(1H)-pyridinone.
24. 6-Ethyl-3-[(3-oxo-1-butenyl)amino]-5-(2-methyl-4-pyridinyl)-2(1H)-pyridinone.
25. 6-Ethyl-3-[(3-oxo-1-butenyl)amino]-5-(3-pyridinyl)-2(1H)-pyridinone.
26. 3-[(3-Oxo-1butenyl)amino]-5-(2,6-dimethyl-4-pyridinyl)-2(1H)-pyridinone.

The usefulness of the compounds of formula I or their pharmaceutically acceptable acid-addition salts as cardiotonic agents is demonstrated by their effectiveness in standard pharmacological test procedures, for example, in causing a significant increase in the contractile force of the isolated cat atria and papillary muscle and in causing a significant increase in the cardiac contractile force in the anesthetized dog with low or minimal changes in heart rate and blood pressure. These test procedures are described in U.S. Pat. No. 4,072,746, issued Feb. 7, 1980.

When tested by the above-described isolated cat atria and papillary muscle procedure at doses of 10, 30 and/or 100 µg./ml., the compounds of formula I were found to cause a significant increase, that is, greater than 25%, in papillary muscle force and a significant increase, that is, greater than 25%, in right atrial force, while causing only a low percentage increase (about one-third or less than the percentage increase in right atrial or papillary muscle force) in right atrial rate. For example, the percentage increases in cat papillary muscle force and right atrial force for 3-[(1-methyl-3-oxo-1-butenyl)amino]-5-(4-pyridinyl)-2(1H)-pyridinone, Example 1 herein, were found to be 32% and 19% respectively when tested at 10 µg./ml., 38% and 34% when tested at 30 µg./ml. respectively and 136% and 54% respectively at 100 µg./ml. Similarly, the percentage increases in cat papillary muscle force and right atrial force for 3-[(3-oxo-1-butenyl)amino]-5-(4-pyridinyl)-2(1H)-pyridinone, Example 2 herein, were found to be 24% and 34% respectively at 10 µg./ml., 34% and 58% respectively at 30 µg./ml. and 56% and 83% respectively at 100 µg./ml.

The present invention includes within its scope a cardiotonic composition for increasing cardiac contractility, said composition comprising a pharmaceutically acceptable carrier and, as the active component thereof, the cardiotonic compound of formula I or pharmaceutically acceptable acid-addition salt thereof. The invention also includes within its scope and method for increasing cardiac contractility in a patient requiring such treatment which comprises administering to such patient a cardiotonically effective amount of said compound of formula I or pharmaceutically acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilizing, preserving, wetting, emulsifying and dispersing agents.

They may be sterilized, for example, by filtration through a bacteria-retaining filter, by incorporation of sterilizing agents in the compositions, by irradiation or by heating. They may also be manufactured in the form of sterile solid compositions which can be dissolved in sterile water or some other sterile injectable medium immediately before use.

The percentages of active component in the said composition and method for increasing cardiac contractility may be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. A compound having the formula

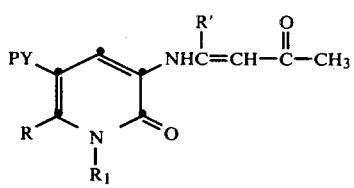

or acid-addition salt thereof, where R' is hydrogen or methyl, $R_1$ and R are each hydrogen or lower-alkyl, PY is 4-pyridinyl or 3-pyridinyl, or 4-pyridinyl or 3-pyridinyl having one or two lower-alkyl substituents.

2. A compound according to claim 1 where PY is 4- or 3-pyridinyl, R and R' are each hydrogen or methyl and $R_1$ is hydrogen.

3. A compound according to claim 1 where PY is 4-pyridinyl, R is hydrogen or methyl, $R_1$ is hydrogen and R' is methyl.

4. 3-[(3-Oxo-1-butenyl)amino]-5-(4-pyridinyl)-2(1H)-pyridinone according to claim 1 or acid-addition salt thereof.

5. 3-[(1-Methyl-3-oxo-1-butenyl)amino]-5-(4-pyridinyl)-2(1H)-pyridinone according to claim 1 or acid-addition salt thereof.

6. A cardiotonic composition for increasing cardiac contractility, said composition comprising a pharmaceutically acceptable carrier and, as the active component thereof, a cardiotonically effective amount of the compound of claim 1 or a pharmaceutically acceptable acid-addition salt thereof.

7. A composition according to claim 6 where the active component is the compound of claim 4.

8. A composition according to claim 6 where the active component is the compound of claim 5.

9. The method for increasing cardiac contractility in a patient requiring such treatment which comprises administering orally or parenterally in solid or liquid dosage form to such patient a cardiotonically effective amount of the compound of claim 1 or pharmaceutically acceptable acid-addition salt thereof.

10. The method according to claim 9 where the active component is the compound of claim 4.

11. The method according to claim 9 where the active component is the compound of claim 5.